US009198500B2

(12) United States Patent
Davis

(10) Patent No.: US 9,198,500 B2
(45) Date of Patent: Dec. 1, 2015

(54) PORTABLE SELF POWERED LINE MOUNTABLE ELECTRIC POWER LINE AND ENVIRONMENT PARAMETER MONITORING TRANSMITTING AND RECEIVING SYSTEM

(71) Applicant: Murray W. Davis, Grosse Pointe Woods, MI (US)

(72) Inventor: Murray W. Davis, Grosse Pointe Woods, MI (US)

(*) Notice: Subject to any disclaimer, the term of this patent is extended or adjusted under 35 U.S.C. 154(b) by 0 days.

(21) Appl. No.: 14/046,242

(22) Filed: Oct. 4, 2013

(65) Prior Publication Data

US 2014/0173891 A1 Jun. 26, 2014

Related U.S. Application Data

(60) Provisional application No. 61/740,517, filed on Dec. 21, 2012.

(51) Int. Cl.
*G01R 5/26* (2006.01)
*G01R 19/32* (2006.01)
(Continued)

(52) U.S. Cl.
CPC ............ *A46B 9/028* (2013.01); *G01B 11/0616* (2013.01); *G01D 11/30* (2013.01); *G01K 13/00* (2013.01); *G01N 27/223* (2013.01); *G01R 1/20* (2013.01); *G01R 1/22* (2013.01); *G01R 19/0084* (2013.01); *G01R 19/0092* (2013.01); *G01R 31/08* (2013.01); *G01R 31/086* (2013.01); *G01R 31/40* (2013.01); *G01W 1/14* (2013.01); *H01F 27/02* (2013.01); *H01F 27/22* (2013.01); *H01F 38/30* (2013.01); *H01R 4/28* (2013.01);
(Continued)

(58) Field of Classification Search
CPC ................................ G01R 15/186; G01R 1/22
USPC .................................................. 324/106, 127
See application file for complete search history.

(56) References Cited

U.S. PATENT DOCUMENTS 2,306,117 A     12/1942  Dunlap
3,253,215 A *   5/1966   Moakler et al. ............... 324/529
(Continued)

FOREIGN PATENT DOCUMENTS

CN           202041573        11/2011

OTHER PUBLICATIONS

Pradhan, et al., Fault Direction Estimation in Radial Distribution System Using Phase Change in Sequence Current, IEEE Transactions on Power Delivery, vol. 22, No. 4, pp. 2065-2071, Oct. 2007.
(Continued)

*Primary Examiner* — Patrick Assouad
(74) *Attorney, Agent, or Firm* — Carlson, Gaskey & Olds, P.C.

(57) ABSTRACT

A device for attaching to an electric power line conductor includes a housing with an opening for accepting the power line conductor and a first jaw assembly and a second jaw assembly. The first jaw assembly and the second jaw assembly are located within the housing and are configured to engage the power line conductor. The first jaw assembly is fixed relative to the housing and the second jaw assembly is movable relative to the housing. A first magnetic core is movable relative to the first jaw assembly and a second magnetic core is fixed to the second jaw assembly. The first magnetic core and the second magnetic core are configured to surround the power line. An actuator is connected to the second jaw assembly and is configured to move the second jaw assembly relative to the first jaw assembly.

22 Claims, 14 Drawing Sheets

(51) Int. Cl.

| | | |
|---|---|---|
| G01R 21/02 | (2006.01) | |
| G01R 21/14 | (2006.01) | |
| A46B 9/02 | (2006.01) | |
| H02G 1/02 | (2006.01) | |
| G01B 11/06 | (2006.01) | |
| G01W 1/14 | (2006.01) | |
| G01R 1/20 | (2006.01) | |
| G01R 19/00 | (2006.01) | |
| G01R 31/08 | (2006.01) | |
| G01N 27/22 | (2006.01) | |
| H01F 38/30 | (2006.01) | |
| H04N 5/225 | (2006.01) | |
| G01D 11/30 | (2006.01) | |
| G01K 13/00 | (2006.01) | |
| H01F 27/02 | (2006.01) | |
| H01F 27/22 | (2006.01) | |
| H01R 4/28 | (2006.01) | |
| G01R 1/22 | (2006.01) | |
| G01R 31/40 | (2014.01) | |
| H04N 7/18 | (2006.01) | |
| G01R 15/18 | (2006.01) | |

(52) U.S. Cl.
CPC ............. *H02G1/02* (2013.01); *H04N 5/2252* (2013.01); *H04N 7/181* (2013.01); *A46B 2200/3073* (2013.01); *G01R 15/186* (2013.01); *Y10T 29/49117* (2015.01)

(56) References Cited

U.S. PATENT DOCUMENTS

| | | | |
|---|---|---|---|
| 3,622,867 A | | 11/1971 | Topper et al. |
| 3,678,372 A | | 7/1972 | Elder |
| 3,820,106 A | | 6/1974 | Yamashita et al. |
| 4,032,842 A | | 6/1977 | Green et al. |
| 4,052,000 A | | 10/1977 | Honikman |
| 4,053,830 A | | 10/1977 | Porter |
| 4,061,963 A | | 12/1977 | Green |
| 4,234,863 A | * | 11/1980 | Shumway et al. ............ 336/90 |
| 4,242,930 A | | 1/1981 | Myers et al. |
| 4,268,818 A | | 5/1981 | Davis et al. |
| 4,326,316 A | | 4/1982 | Dolenti |
| 4,420,752 A | | 12/1983 | Davis et al. |
| 4,499,417 A | | 2/1985 | Wright et al. |
| 4,546,340 A | | 10/1985 | Kuchuris |
| 4,728,887 A | | 3/1988 | Davis |
| 4,746,241 A | | 5/1988 | Burbank |
| 4,801,937 A | | 1/1989 | Fernandes |
| 4,806,855 A | | 2/1989 | Davis |
| 4,827,272 A | | 5/1989 | Davis |
| 5,029,101 A | | 7/1991 | Fernandes |
| 5,140,257 A | | 8/1992 | Davis |
| 5,341,088 A | | 8/1994 | Davis |
| 5,426,360 A | | 6/1995 | Maraio et al. |
| 5,565,783 A | * | 10/1996 | Lau et al. ............ 324/522 |
| 5,652,506 A | * | 7/1997 | Sorenson et al. ......... 324/117 R |
| 5,703,568 A | | 12/1997 | Hegyi |
| 5,796,259 A | | 8/1998 | Dickmander |
| 5,883,511 A | | 3/1999 | Foster |
| 6,144,017 A | | 11/2000 | Millett et al. |
| 6,151,065 A | | 11/2000 | Steed et al. |
| 6,157,160 A | | 12/2000 | Okawa et al. |
| 6,713,670 B2 | | 3/2004 | Stern et al. |
| 6,741,069 B1 | | 5/2004 | Klemar et al. |
| 6,924,732 B2 | | 8/2005 | Yohoo |
| 7,030,593 B2 | | 4/2006 | Pinkerton et al. |
| 7,127,972 B2 | | 10/2006 | Klein et al. |
| 7,310,109 B2 | | 12/2007 | Dottling et al. |
| 7,412,338 B2 | | 8/2008 | Wynans et al. |
| 7,432,787 B2 | | 10/2008 | Muench et al. |
| 7,545,140 B2 | | 6/2009 | Humphreys et al. |
| 7,557,563 B2 | * | 7/2009 | Gunn et al. ............ 324/127 |
| 7,570,045 B2 | | 8/2009 | Wolfe et al. |
| 7,579,824 B2 | | 8/2009 | Rea |
| 7,706,596 B2 | | 4/2010 | Garvey |
| 8,144,445 B2 | | 3/2012 | Caggiano et al. |
| 8,184,015 B2 | | 5/2012 | Lilien et al. |
| 8,203,328 B2 | | 6/2012 | Bose et al. |
| 8,300,922 B1 | | 10/2012 | Garvey, III |
| 8,400,504 B2 | | 3/2013 | Al-Duwaish et al. |
| RE44,256 E | | 6/2013 | Bright et al. |
| 8,536,857 B2 | * | 9/2013 | Nero, Jr. ............ 324/119 |
| 8,686,302 B2 | | 4/2014 | Brasher et al. |
| 2003/0052687 A1 | | 3/2003 | McQueeney et al. |
| 2004/0012678 A1 | | 1/2004 | Li |
| 2006/0060007 A1 | | 3/2006 | Mekhanoshin |
| 2006/0125469 A1 | | 6/2006 | Hansen |
| 2008/0077336 A1 | | 3/2008 | Fernandes |
| 2008/0136403 A1 | | 6/2008 | Deck |
| 2008/0297162 A1 | | 12/2008 | Bright |
| 2009/0009180 A1 | | 1/2009 | Varghai et al. |
| 2009/0207421 A1 | | 8/2009 | Kelly et al. |
| 2009/0212241 A1 | | 8/2009 | McGeoch |
| 2009/0243876 A1 | | 10/2009 | Lilien et al. |
| 2010/0013457 A1 | * | 1/2010 | Nero, Jr. ............ 324/119 |
| 2010/0039090 A1 | | 2/2010 | Sykes |
| 2010/0084920 A1 | | 4/2010 | Banting et al. |
| 2010/0085036 A1 | | 4/2010 | Banting et al. |
| 2011/0101960 A1 | * | 5/2011 | Wang et al. ............ 324/127 |
| 2011/0204879 A1 | | 8/2011 | Peretto |
| 2011/0267673 A1 | | 11/2011 | Agrawal et al. |
| 2012/0086804 A1 | | 4/2012 | Ishibashi et al. |
| 2013/0022078 A1 | | 1/2013 | Phillips et al. |
| 2013/0179079 A1 | | 7/2013 | Lancaster |
| 2013/0205900 A1 | | 8/2013 | Nulty |
| 2013/0221977 A1 | | 8/2013 | Ukil et al. |
| 2013/0328546 A1 | * | 12/2013 | Nero, Jr. ............ 324/119 |
| 2014/0110376 A1 | | 4/2014 | Zahlmann et al. |
| 2014/0123750 A1 | | 5/2014 | Liu et al. |
| 2014/0145858 A1 | | 5/2014 | Miller et al. |

OTHER PUBLICATIONS

Eissa, Evaluation of a New Current Directional Protection Technique Using Field Data, IEEE Transactions on Power Delivery, vol. 20, No. 2, pp. 566-572, Apr. 2005.

Ukil, et al., Smart Distribution Protection Using Current-Only Directional Overcurrent Relay, Innovative Smart Grid Technologies Conference Europe, 2010 IEEE PES, pp. 1-7, 2010.

Recloser, available at http://en.wikipedia.org/wiki/Recloser on Feb. 2, 2012.

Digital protective relay, available at http://en.wikipedia.org/wiki/Digital_protective_relay on Jun. 18, 2012.

* cited by examiner

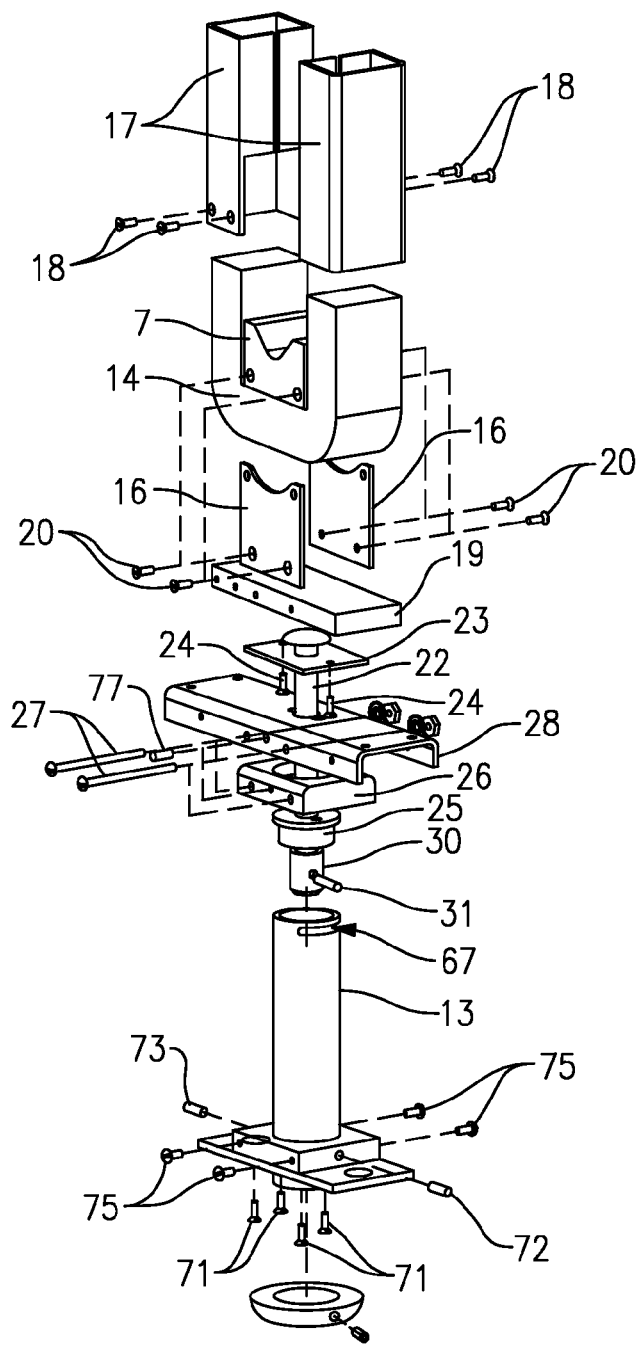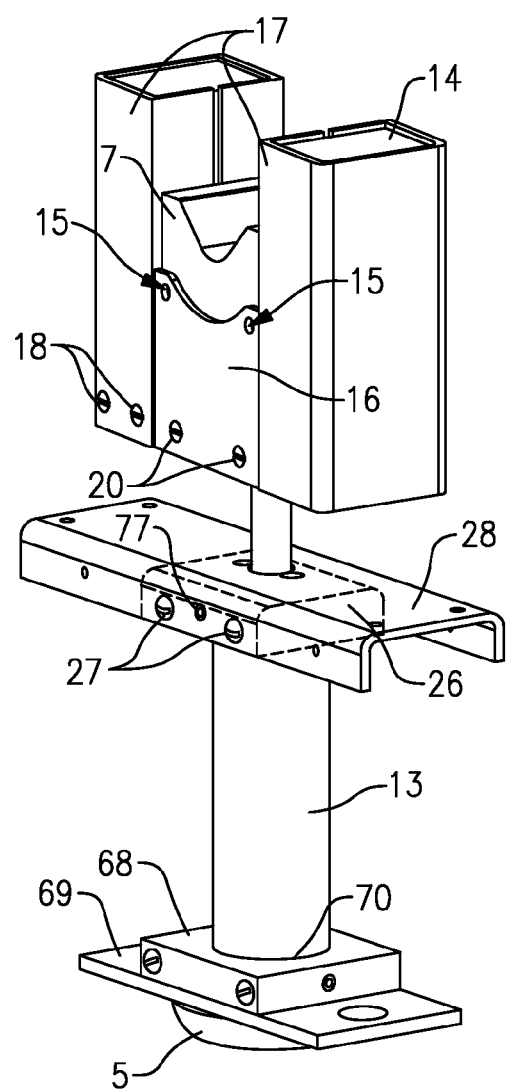
FIG.10
FIG.11

PORTABLE SELF POWERED LINE MOUNTABLE ELECTRIC POWER LINE AND ENVIRONMENT PARAMETER MONITORING TRANSMITTING AND RECEIVING SYSTEM

CROSS-REFERENCE TO RELATED APPLICATIONS

The application claims priority to U.S. Provisional Application No. 61/740,517 which was filed on Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device which is low maintenance and can be constantly powered independent of weather conditions.

SUMMARY

A device for attaching to an electric power line conductor includes a housing with an opening for accepting the power line conductor and a first jaw assembly and a second jaw assembly. The first jaw assembly and the second jaw assembly are located within the housing and are configured to engage the power line conductor. The first jaw assembly is fixed relative to the housing and the second jaw assembly is movable relative to the housing. A first magnetic core is movable relative to the first jaw assembly and a second magnetic core is fixed to the second jaw assembly. The first magnetic core and the second magnetic core are configured to surround the power line. An actuator is connected to the second jaw assembly and is configured to move the second jaw assembly relative to the first jaw assembly.

A method of attaching a device to a power line conductor includes resting a first jaw assembly on a power line conductor with the first jaw assembly fixed relative to a housing. A second jaw assembly is moved toward the first jaw assembly with an actuator. A second magnetic core is moved toward a first magnetic core with the actuator. The second magnetic core is fixed relative to the second jaw assembly and the first magnetic core is moveable relative to the first jaw assembly. The first magnetic core and the second magnetic core move relative to the first jaw assembly.

These and other features of the disclosed examples can be understood from the following description and the accompanying drawings, which can be briefly described as follows.

BRIEF DESCRIPTION OF THE DRAWINGS

FIG. 10 illustrates an expanded view of the lower magnetic core, example lead screw assembly, and an example hotstick guide tube.

FIG. 11 illustrates the collapsed view of the lower magnetic core, the lead screw assembly, and the hotstick guide tube.

DETAILED DESCRIPTION

Figure 1:
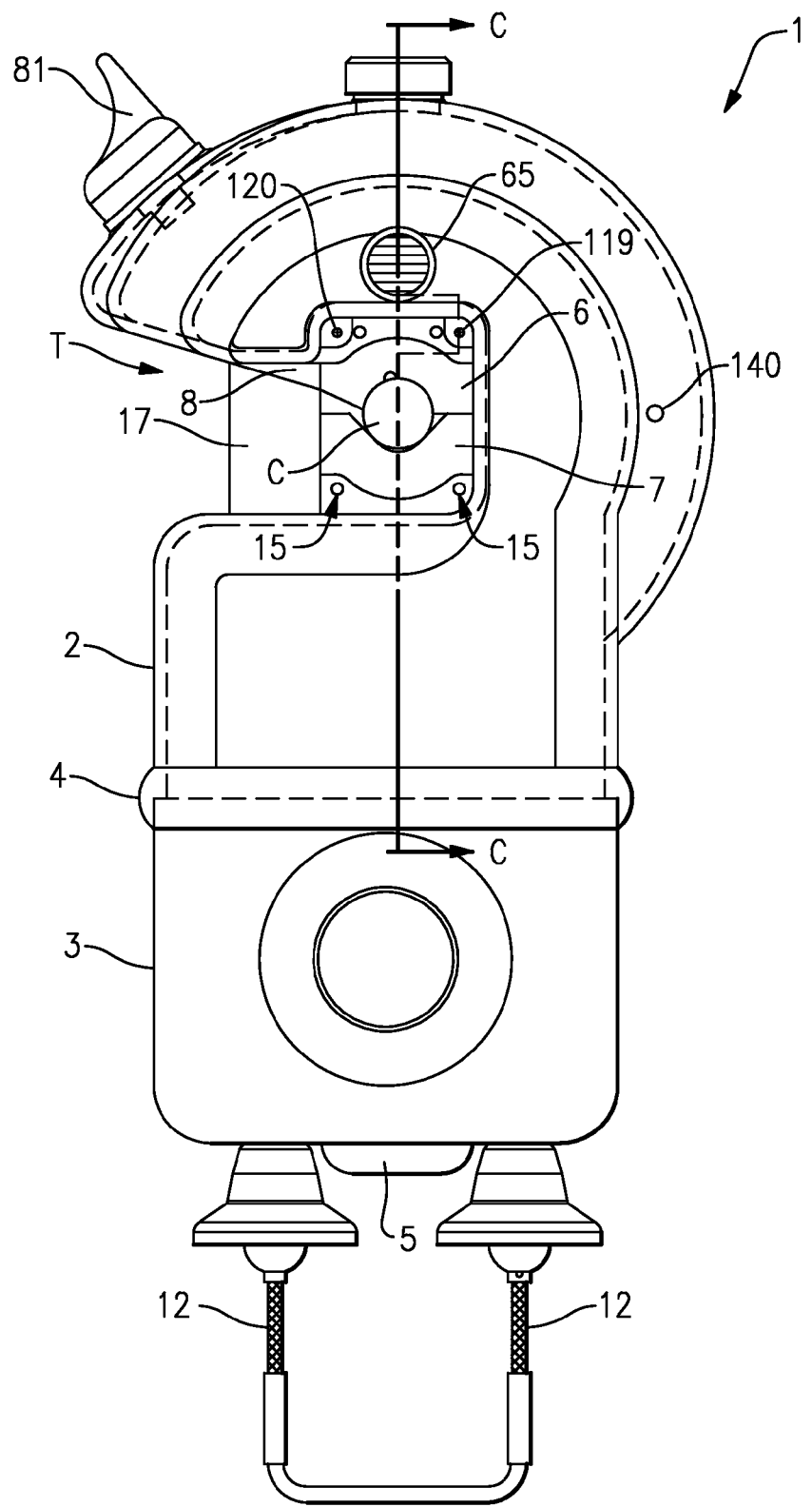
FIG. 1 illustrates a right side view of an example sensor transmitter receiver unit ("STR unit").
Figure 2:
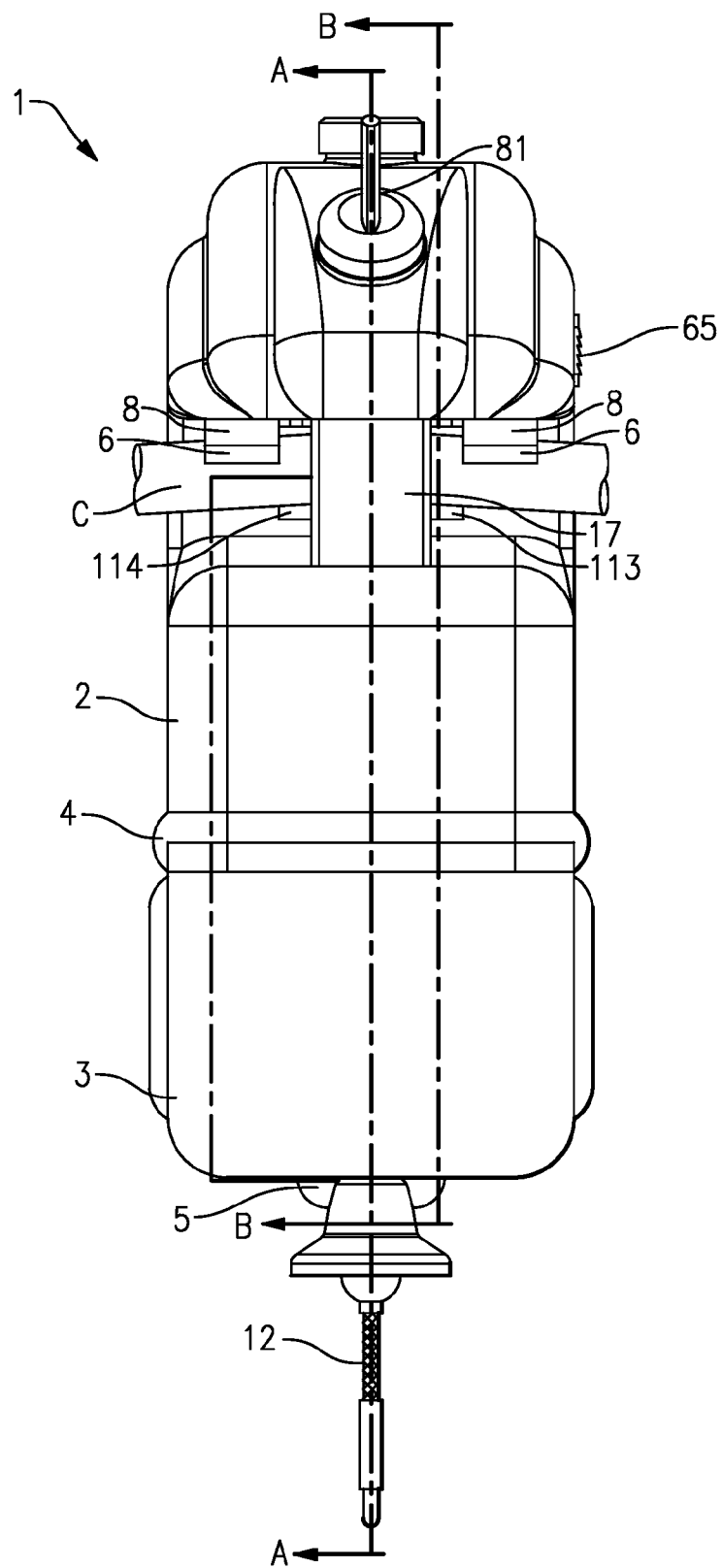
FIG. 2 illustrates a front view of the STR unit of FIG. 1.

FIGS. 1 and 2 illustrate an example sensor transmitter receiver unit ("STR unit") 1 installed on a power line conductor C for measuring and monitoring various parameters of the power line conductor C and its environment. The STR unit 1 is formed from a one piece upper housing 2 and a one piece lower housing 3. The lower housing 3 is accepted into a bead 4 formed on a distal end of the upper housing 2. In this example, the bead 4 which is an integral part of the upper housing 2 is formed by machining a portion of the upper housing 2 to form a groove on the inside of the bead 4. The lower housing 3 is secured to the bead 4 and the upper housing 2 by a collar 5. The collar 5 attaches to a hotstick guide tube 13 (FIG. 3) that is secured to the upper housing 2 and extends through the lower housing 3.

In one example, the upper housing 2 and the lower housing 3 are made of aluminum or other suitable electrically conductive material. The material chosen should accommodate subassembly installation without the use of external surface fasteners which could generate corona discharges due to high voltage being applied to the upper housing 2 and the lower housing 3. The upper housing 2 has the advantage of reducing the number of mating surfaces and eliminating mismatches between multiple cast parts which can generate corona discharges and audible noise due to slightly offset sharp edges of the mating surfaces of the adjacent castings.

Figure 3:
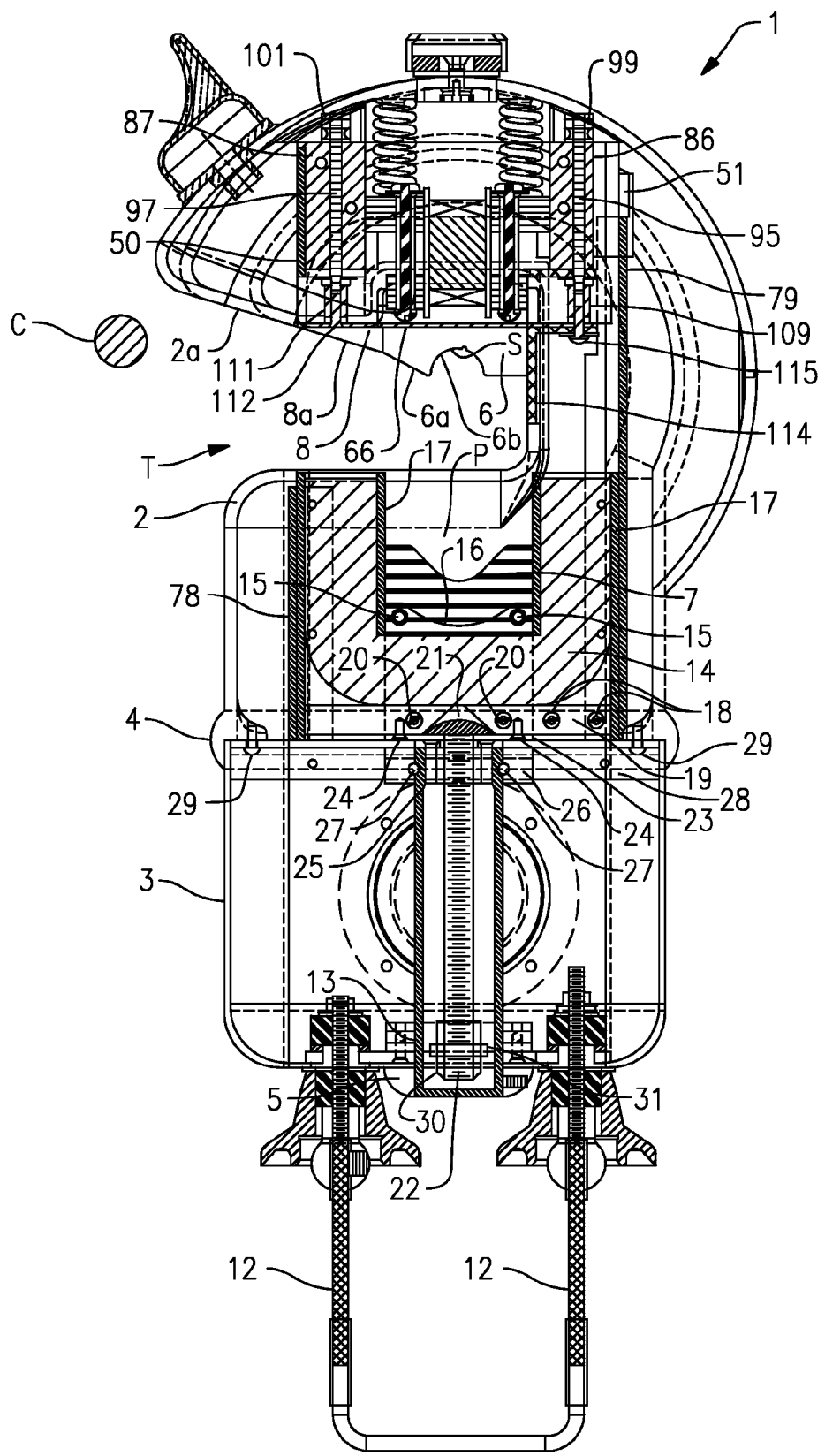
FIG. 3 illustrates a cross-sectional view taken along line A-A of FIG. 2.
Figure 4:
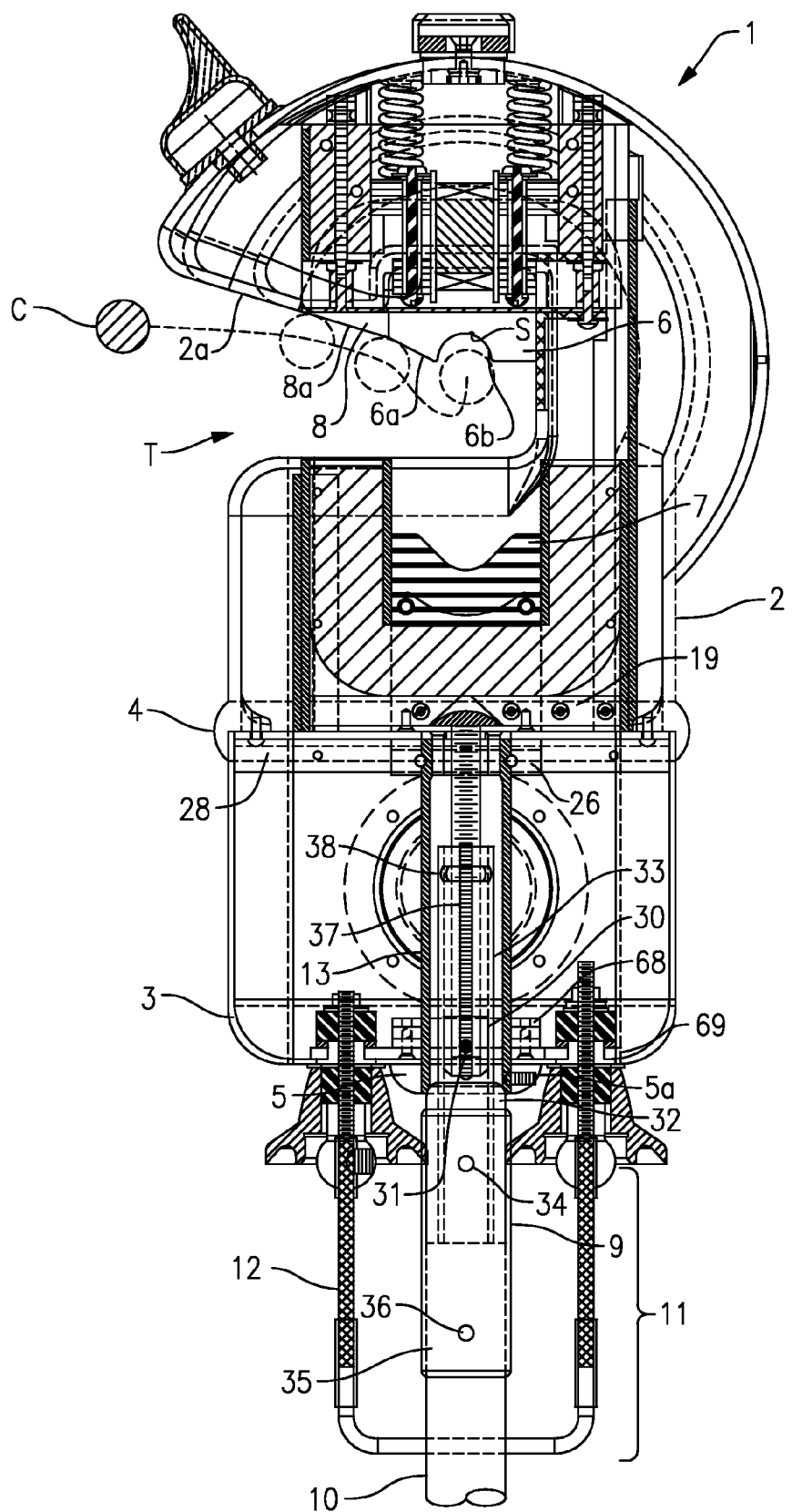
FIG. 4 illustrates a cross-sectional view taken along line A-A of FIG. 2 with an example hotstick.

Referring to FIGS. 3 and 4, before the STR unit 1 is clamped onto the conductor C, a lower jaw 7 is moved to its fully lowered position spaced from upper jaws 6. This allows the conductor C to pass from position "A" of FIG. 3 through a throat T on the left side of the upper housing 2 and onto the upper jaws 6 in position "B" as shown in FIG. 5.

With the lower jaw 7 of the STR unit 1 in its fully lowered position, a specially designed hotstick 10 is inserted into the bottom of the STR unit 1 and inside the hotstick guide tube 13. In this example, the hotstick 10 is made of an electrically insulated material such as fiberglass. The hotstick 10 includes a hotstick driver assembly 9 (FIG. 4) attached to the hotstick 10 with a pin 36. The hotstick 10 provides the required electrical insulation between the hands of the linemen and the energized conductor C. A flexible stirrup assembly 11 (FIG. 4) contains a flexible braided conductor 12 which bends out of the way to allow the hotstick driver assembly 9 to enter a hole in the collar 5. As mentioned earlier, the collar 5 secures the lower housing 3 to the bead 4 on the upper housing 2. The collar 5 is fastened to the hotstick guide tube 13 using the set screw 5a which is screwed into the collar 5 and into a hole in the hotstick guide tube 13.

With the hotstick 10 and the hotstick driver assembly 9 fully engaged inside the hotstick guide tube 13, the STR unit 1 can be lifted by the lineman with the hotstick 10 onto the conductor C while maintaining the STR unit 1 securely attached to the hotstick 10.

Figures 5, 5A:
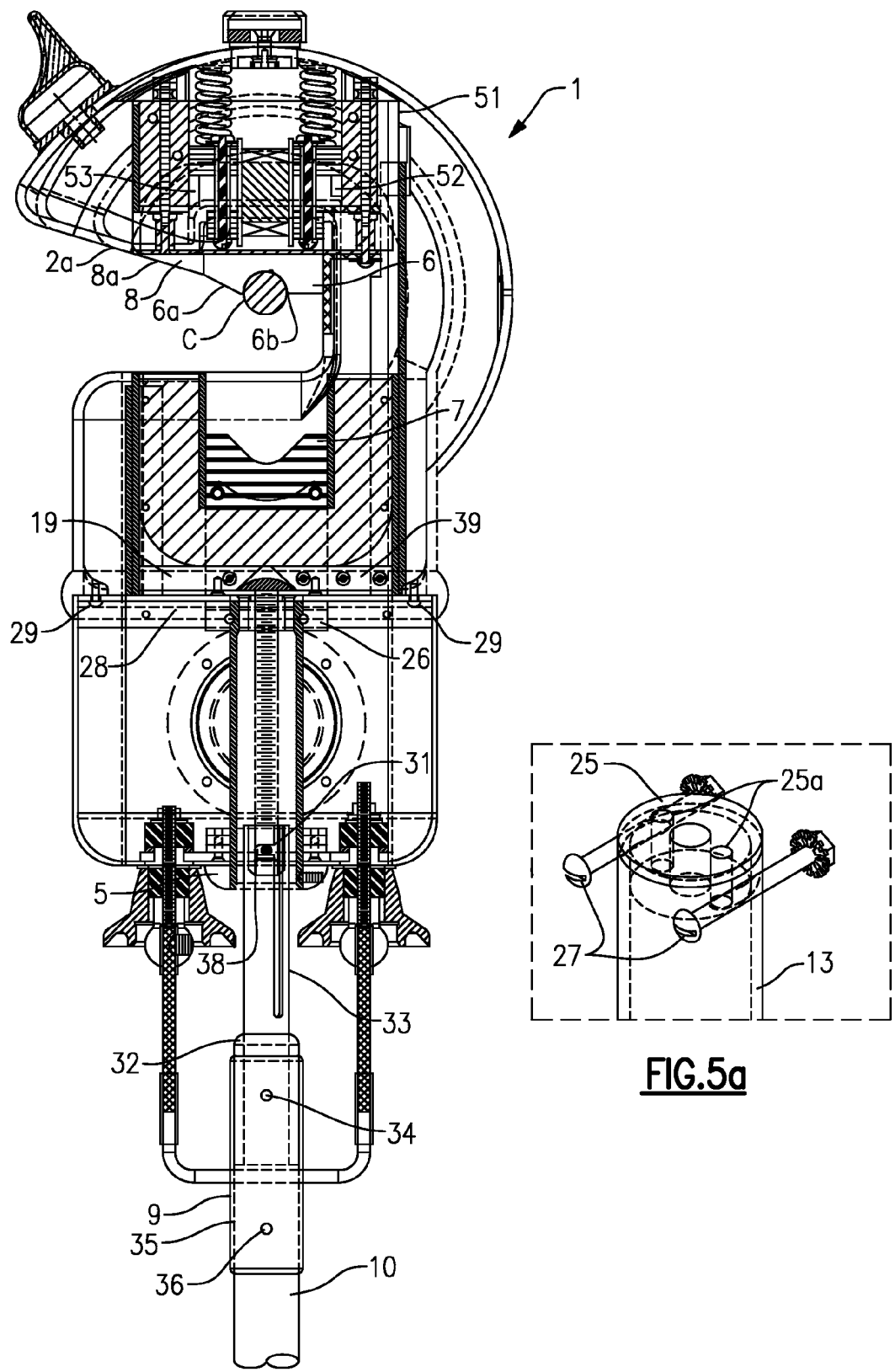
FIG. 5 illustrates another cross-sectional view taken along line A-A of FIG. 2 with the example hotstick.
FIG. 5a illustrates an enlarged view of a keyhole slot.
Figure 14:
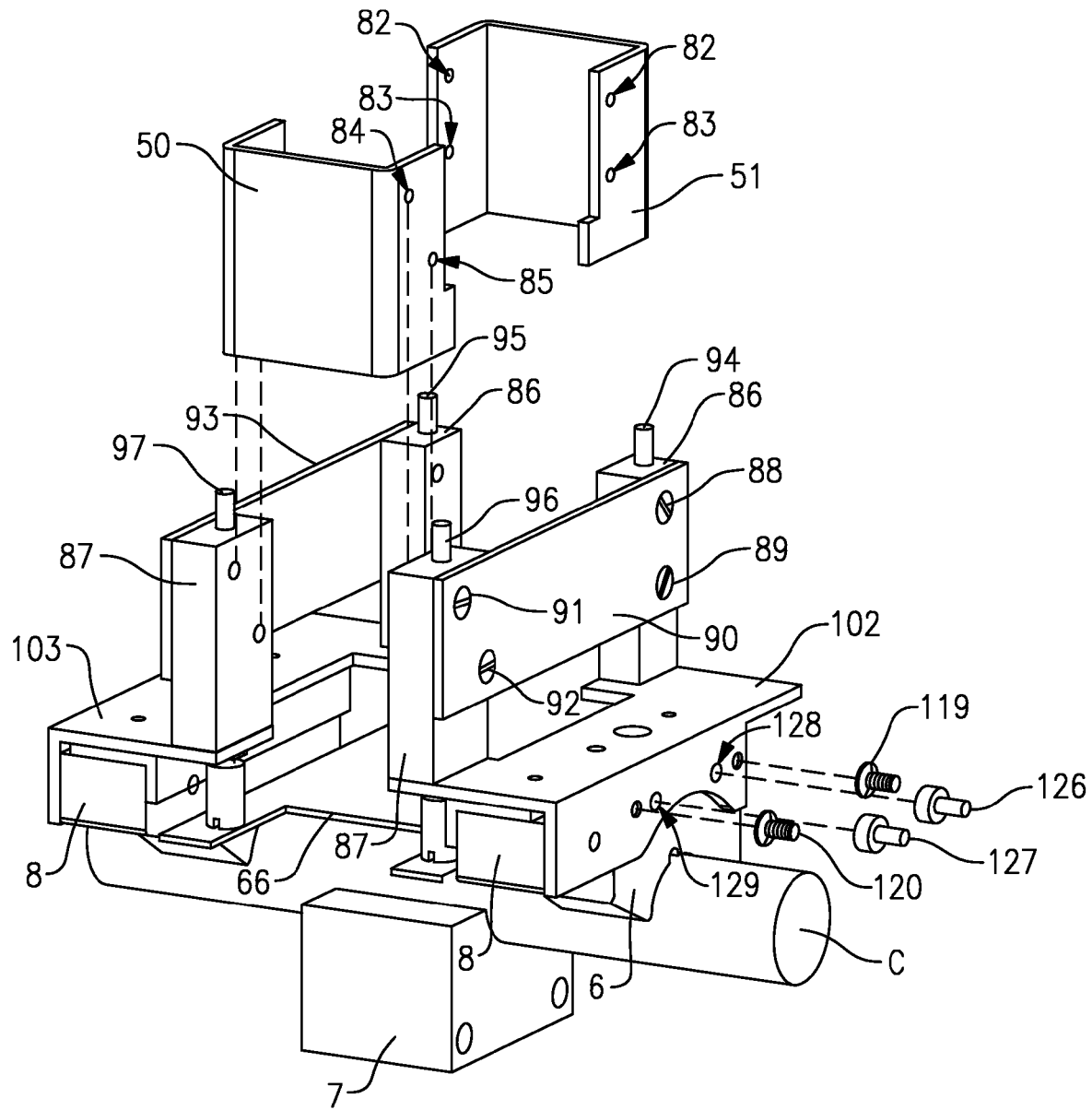
FIG. 14 illustrates an exploded view of example support blocks mounting the upper magnetic core subassembly and example upper and lower jaws.

The upper housing 2 includes two jaw inserts 8, shown in FIGS. 5 and 14, located adjacent the throat T and the upper jaws 6. The two jaw inserts 8 include inclined surfaces 8a and the upper jaws 6 include inclined surfaces 6a. The angle of incline of the inclined surfaces 8a matches the angle of the incline of an inclined surface 2a on the upper housing 2.

The angle of the inclined surfaces 6a is steeper than the angle of the inclined surfaces 8a and the inclined surface 2a to aid in installing the STR Unit 1 on the conductor C. As the conductor C slides across the inclined surfaces 2a and 8a and reaches the steeper incline of the inclined surface 6a, the STR unit 1 will bounce slightly upward and land in a circular notch 6b of the upper jaws 6 (See FIG. 4). This allows a conductor temperature sensor to be mounted vertically and in the middle inside the upper jaws 6 and initially extends slightly below the circular notch 6b for the upper portion of the conductor C. The two different inclined surfaces 6a and 8a of the jaw inserts 8 and upper jaws 6 prevent the conductor temperature sensor S, shown in FIGS. 3 and 4, from becoming damaged since the conductor C firmly lands vertically in the circular notch 6b of the upper jaws 6 and pushes the conductor temperature sensor S up to the inside surface of the circular notch 6b.

In FIG. 3, the lower jaw 7 is located in a pocket P between two legs of a lower magnetic core 14. The lower jaw 7 is held in place with two spring pins 132 and 133 (FIG. 15) located in the lower jaw 7 that snap into two holes 15 in a lower jaw holder 16 (FIGS. 10 and 11) which is attached to a bottom block 19 using two screws 20 (FIG. 3). The bottom block 19 is located adjacent the base of the upper housing 2.

Two identical electrically conductive lower core covers 17 partially surround the two legs of the lower magnetic core 14. The lower core covers 17 are attached to the bottom block 19 on each side of the lower jaw holder 16 using screws 18 of FIG. 3 on the front right side and one set of the screws 18 on the back left side (not shown). The front and back lower jaw holders 16 are both held in place by the four screws 20, two in the front and two in the back. The two legs of the lower magnetic core 14 are totally encased by the two lower core covers 17 and the front and back lower jaw holders 16. Therefore, the lower magnetic core 14 is not exposed to any moisture, such as from rain, snow, and ice that could enter through the throat T of the upper housing 2 (FIG. 3).

The bottom block 19 contains a conical hole 21 in the center which provides a very low friction bearing surface for the semi-circular top of a lead screw 22 (FIG. 3). The lead screw 22 is held in the conical hole 21 with a retainer plate 23 which has a hole in the middle the size of the lead screw 22 diameter and is fastened to the bottom block 19. The lead screw 22 is threaded into the center of a threaded bushing 25. The threaded bushing 25 has a reduced diameter cylindrical lower portion which fits inside the hotstick guide tube 13 and a larger diameter cylindrical top portion of the threaded bushing 25 is supported on the upper end of the hotstick guide tube 13. Both the threaded bushing 25 and the hotstick guide tube 13 are attached to a hotstick guide support 26 using two large through bolts 27 and nuts which are placed through the holes in a bottom support 28.

Referring to FIG. 2, the upper jaws 6 include two spaced apart jaws and the lower jaw 7 includes a single jaw aligned between the two spaced apart upper jaws 6. When lower jaw 7 is clamped onto the conductor C, the conductor C is bent slightly upward as the lower jaw 7 extends upward between the upper jaws 6 creating a bending moment in the conductor C. The bending moment in the conductor C prevents the STR unit 1 from sliding down the conductor C, especially when the STR unit 1 is mounted at the point of attachment adjacent a utility pole or tower where the slope of the conductor C is at its maximum value. Preventing the upper jaws 6 and the lower jaw 7 from sliding down the conductor C at the point of attachment is necessary when the STR unit is being used to measure sag of the power line conductor.

Referring to FIGS. 5 and 5a, the bottom support 28 includes an upside down "U" shaped cross member and is fastened at each end to the upper housing with two large threaded screws 29 on each side. The threaded bushing 25 has two small vertical holes 25a drilled through the threaded bushing 25 on each side of the threaded hole in the middle for the lead screw 22. The vertical holes 25a are countersunk on the top and provide drainage paths for fluid, such as rain water, that can accumulate underneath the bottom block 19 and on top of the bottom support 28 (FIG. 5a). The water then drains through the two vertical holes 25a in the threaded bushing 25 and drops on the inside of the hotstick guide tube 13 and out the bottom of the STR unit 1. Therefore, water will not leak into the lower housing 3.

Figure 6:
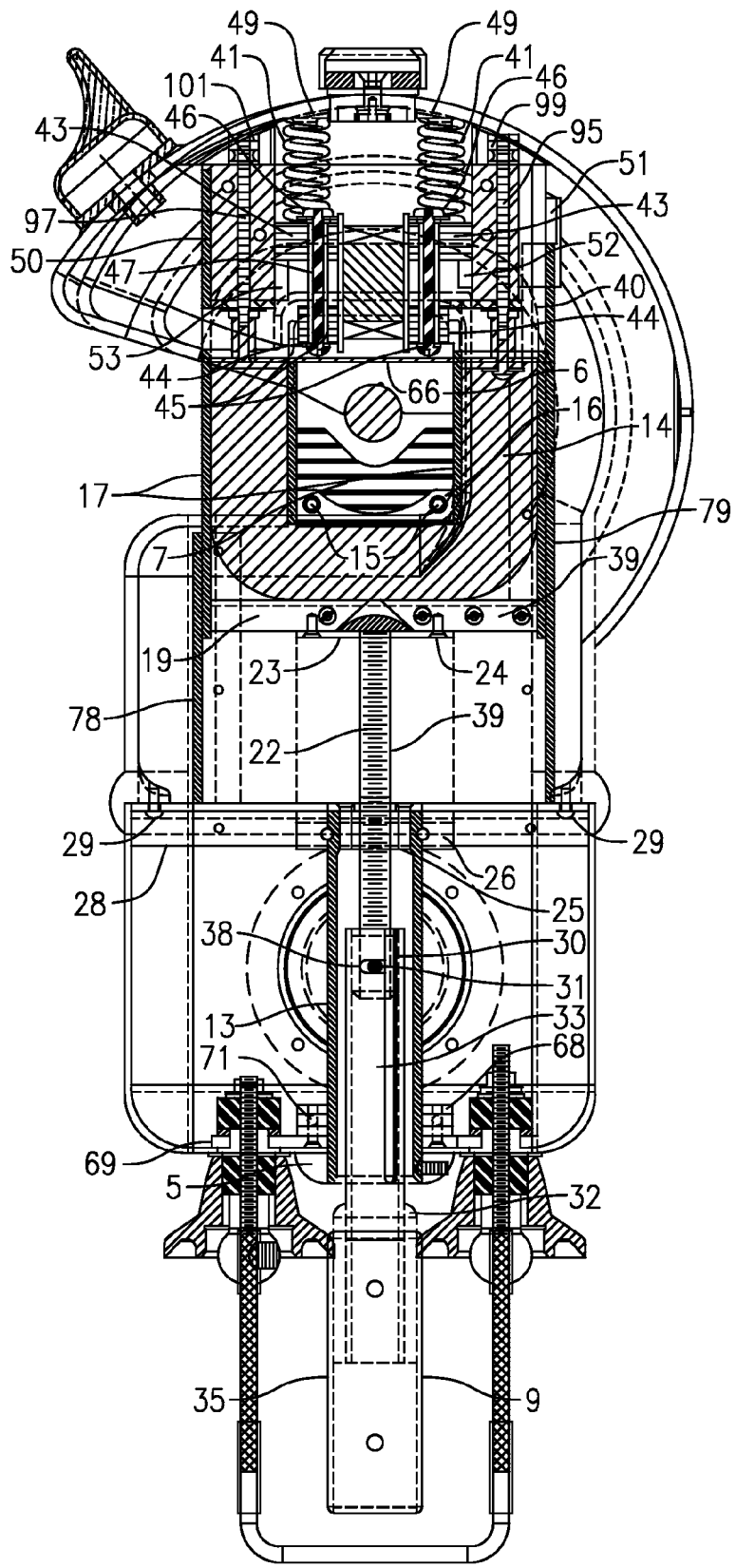
FIG. 6 illustrates another cross-sectional view taken along line A-A of FIG. 2 engaging a conductor.

Referring to FIG. 6, the lead screw 22 has a small diameter hotstick guide 30 which is threaded on the inside and is screwed on the bottom of the lead screw 22. A pin 31 keeps the hotstick guide 30 from turning on the lead screw 22. The hotstick guide 30 prevents the inside of a hotstick lead screw driver 33 from coming into contact with the threads on the lead screw 22 and damaging the internal bore of the lead screw driver 33. It also guides the lead screw driver 33 onto the lead screw 22. When the pin 31 engages the lead screw driver 33 the STR unit 1 is ready for installation on the conductor C.

The hotstick driver assembly 9 includes the lead screw driver 33, a hotstick driver coupling 32, a rivet 34, a hotstick sleeve 35, the pin 36, and the hotstick 10. The hotstick 10 of FIG. 4 rests on the rounded portion of the hotstick driver coupling 32 and the rounded inside bottom of the hotstick guide tube 13. This prevents the lead screw driver 33 from applying pressure to the threaded bushing 25 upon installation of the STR unit 1 on the conductor C. The lead screw driver 33 and the hotstick driver coupling 32 are each fastened to the hotstick sleeve 35 by the rivet 34 and the hotstick sleeve 35 is attached to the hotstick 10 with the pin 36. A long narrow vertical slot in the lead screw driver 33 allows the pin 31 of the lead screw 22 to be engaged with the lead screw driver 33 and is free to slide up or down in the vertical slot 37 as the lead screw is turned to tighten the lower jaw 7 on the conductor C or to loosen the lower jaw 7 from the conductor C to remove the STR unit 1.

When the hotstick driver assembly 9 is engaged with the lead screw 22 as shown in in FIG. 4, the STR unit 1 is raised to position "A" relative to the height of the conductor C. The STR unit 1 is then moved toward the conductor C so that the conductor C passes through the throat T of the upper housing 2 and into position "B" as shown in FIG. 5. Once the STR unit 1 is fully supported by the conductor C in position "B", the hotstick driver assembly 9 is turned clockwise by the installer with the hotstick 10 and allowed to drop down from its position in FIG. 4 to a lower position as in FIG. 5. A horizontal keyhole slot 38 of the lead screw driver 33 is now engaged with the pin 31 of the lead screw 22. With the pin 31 in the horizontal keyhole slot 38, the hotstick driver assembly 9 and the hotstick 10 are secured to the STR unit 1.

In this example, an opening and closing mechanism 39 of FIG. 6 extends the lower jaw 7 upward to secure the STR unit 1 on the conductor C. Additionally, the opening and closing mechanism 39 can also retract the lower jaw 7 to remove the STR unit 1 from the conductor C. The opening and closing mechanism 39 includes the lower magnetic core 14, the lower core covers 17, the lower jaw holders 16, the lower jaw 7, spring pins 132 and 133, the bottom block 19, the retainer plate 23, two fasteners 24, the lead screw 22, the hotstick guide 30, and the pin 31.

FIG. 6 illustrates the keyhole slot 38 on the lead screw driver 33 engaged with the pin 31 on the lead screw 22. As the lead screw 22 is turned clockwise, the opening and closing mechanism 39 moves the lower magnetic core 14 toward an upper magnetic core 40. The upper magnetic core 40 has two large compression springs 41 to bias the upper magnetic core 40 downward. The compression springs 44 provide pressure to hold both the upper magnetic core 40 and the lower magnetic core 14 together to reduce the magnetic reluctance caused by air gaps 54 (FIG. 8) between the upper magnetic core 40 and the lower magnetic core 14.

The hotstick driver assembly 9 can continue to be turned clockwise even after the lower magnetic core 14 begins to mate with the upper magnetic core 40 because the compression springs 41 compress at the top of the upper magnetic core 40. The clockwise motion of the hotstick driver assembly 9 can be achieved either manually or with a battery powered drill or another rotating device, until the lower jaw 7 is tightened onto the conductor C. After the STR unit 1 is mounted on the conductor C, the hotstick 10 is turned slightly to the left, or counterclockwise, and the pin 31 will become disengaged from the horizontal portion of the keyhole slot 38. The hotstick 10 is then free to be removed when the pin 31 aligns with the vertical slot 37.

Figure 7:
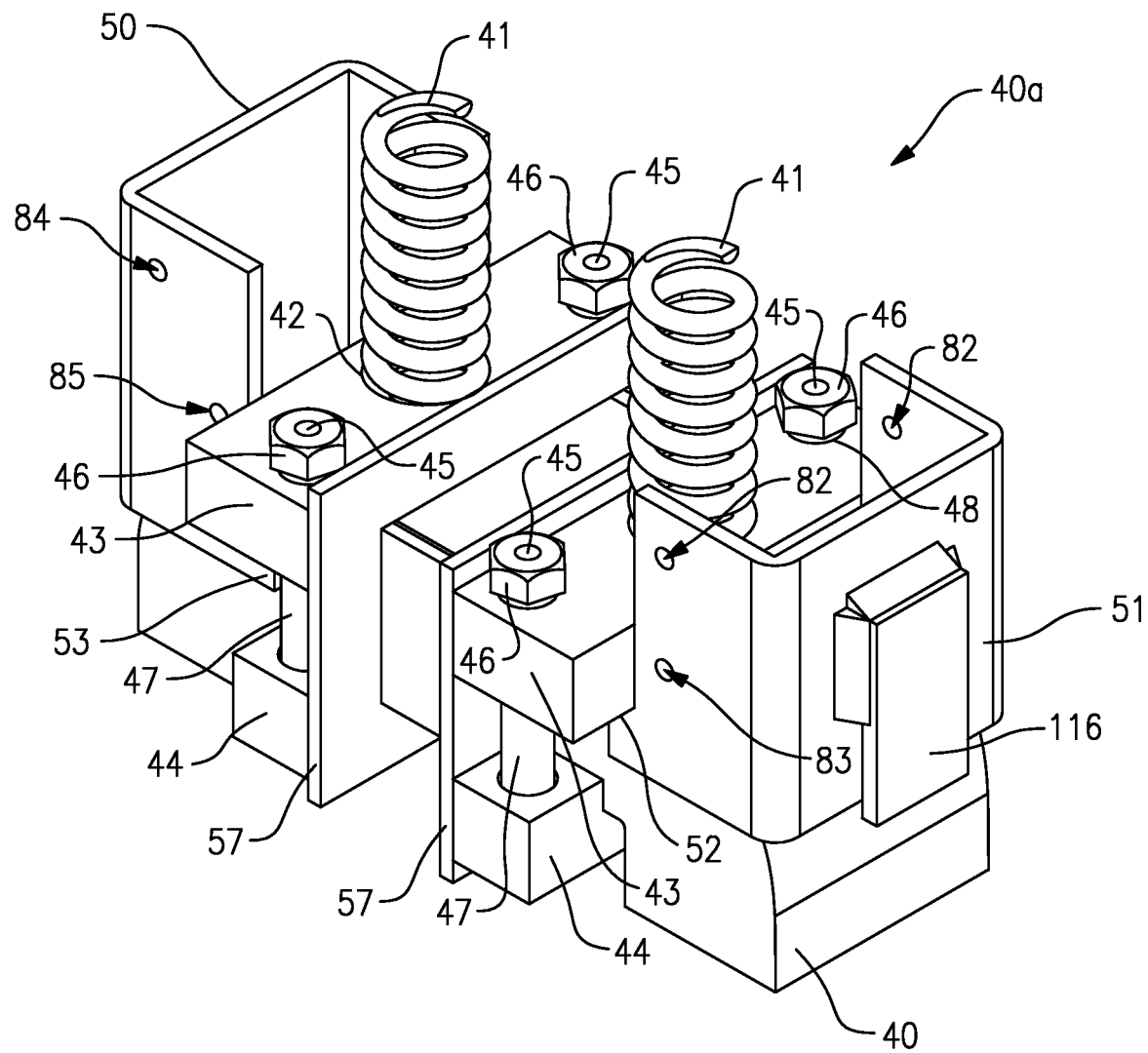
FIG. 7 illustrates an example upper magnetic core subassembly.
Figure 8:
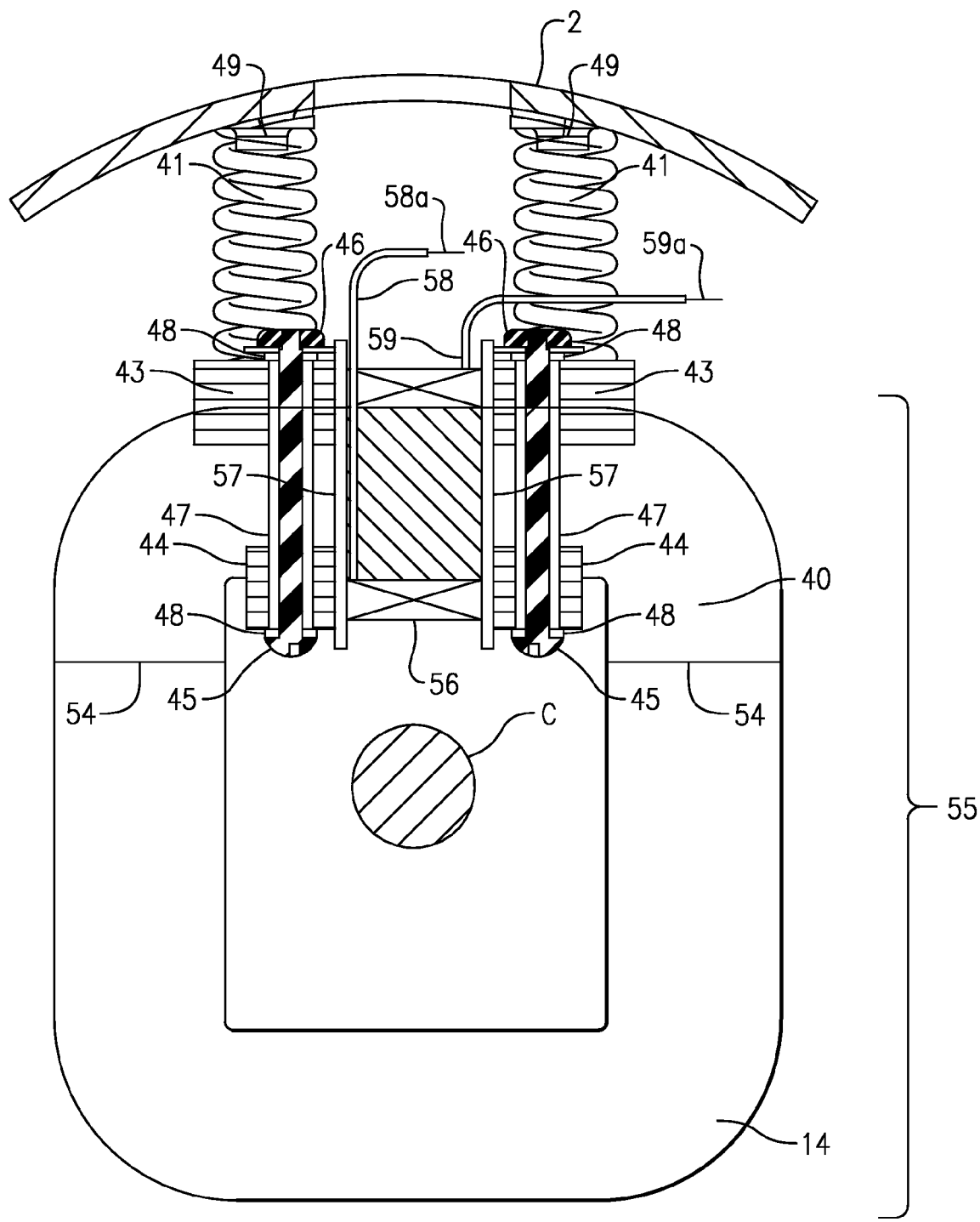
FIG. 8 illustrates an expanded view of an example upper magnetic core and an example lower magnetic core surrounding the conductor and an example power supply transformer.

FIGS. 7 and 8 illustrate the bottom of the compression springs 41 are held in alignment in two cylindrical pockets 42 of two identical horizontal upper core blocks 43 which are each used to clamp the upper magnetic core 40 to two identical magnetic horizontal lower core blocks 44. The top of the compression springs 41 are held in place with two projections 49 extending downward on the inside of the upper housing 2. The compression springs 41 are totally enclosed by the upper housing 2 and are protected from the adverse weather which can cause corrosion. The air gaps 54 between the upper and lower magnetic cores 40 and 14 are totally enclosed by the upper housing 2 which prevents the air gaps 54 from becoming corroded due to moisture from the environment. The horizontal upper core blocks 43 and the horizontal lower core blocks 44 are clamped around the upper magnetic core 40 on each side using two through bolts 45 and two nuts 46 in the front and two through bolts 45 and two nuts 46 located in the back of the upper horizontal core blocks 43 and horizontal lower core blocks 44.

When the two large compression springs 41 push the upper core blocks 43 down, the upper magnetic core 40 is prevented from falling out of a left core shoe 50 and a right core shoe 51, by a step 52 located at the bottom of the right core shoe 51 and a step 53 located at the bottom of the left core shoe 50.

When the lower magnetic core 14 mates with the upper magnetic core 40, the lead screw 22 can be turned further clockwise to move the two upper core blocks 43 away from the steps 52 and 53 and further compress the compression springs 41. The lead screw 22 can continue to be turned clockwise and compress the compression springs 41 until the lower jaw 7 and the upper jaws 6 are tight on the conductor C.

Electrical insulating spools 47 are inserted over each of the through bolts 45 and electrical insulating washers 48 are inserted under the head of each through bolt 45 and under each nut 46. The insulating spools 47 and the insulating washers 48 on each of the through bolts 45 prevent shorted electrically conductive paths around the upper magnetic core 40 which is comprised of the four through bolts 45, four nuts 46, the two electrically conductive upper core blocks 43 and the two lower core blocks 44.

When the upper jaws 6 and the lower jaw 7 are firmly tightened on the conductor C, the compression springs 41 are compressed to their maximum distance, and thus the maximum compressive force is also applied to the lower magnetic core 14 and the upper magnetic core 40. This decreases the size of the air gaps 54 between the lower magnetic core 14 and the upper magnetic core 40 and the magnetic reluctance between the lower magnetic core 14 and the upper magnetic core 40. Depending on the size of the conductor C, varying amounts torque can be applied to the hotstick driver assembly 9 to tighten the opening and closing mechanism 39 on the conductor C.

The physical size and shape of the upper jaws 6 and the lower jaw 7 are designed such that approximately the same compressive force is applied to the upper magnetic core 40 and the lower magnetic core 14. In one example, there are five different sets of upper and lower jaws 6 and 7 that can fit different conductor sizes and types ranging from 0.162 inches in diameter and up to 1.17 inches in diameter. The opening and closing mechanism 39 allows the STR unit 1 to be installed on a wide range of conductor diameters without changing the upper jaws 6 and the lower jaws 7 while maintaining sufficient contact between the upper magnetic core 40 and the lower magnetic core 14 to complete the magnetic circuit of the power supply transformer 55 of the STR unit 1 which derives its power from the current flowing through the conductor C to power a power supply module 60 of FIG. 9. Because the STR unit 1 derives power from the conductor C, batteries or solar cells are not required to power the STR unit 1. The STR unit 1 is powered at all times when current is flowing in the conductor C, even at current levels as low as 6.8 amperes and still process data and transmit data at 1 watt power levels because of the low threshold of the power supply module 60.

Maintaining a minimum magnetic reluctance insures that a power supply transformer 55 (FIGS. 8 and 9) will provide the needed secondary voltage $V_2$ and secondary current $I_2$ to operate the power supply transformer 55, sensor electronics module 63, and transmitter/receiver 64. The power supply transformer 55 includes the upper magnetic core 40, the lower magnetic core 14, and a coil winding 56. The upper magnetic core and the lower magnetic core form a window W for accepting the conductor C.

Figure 12:
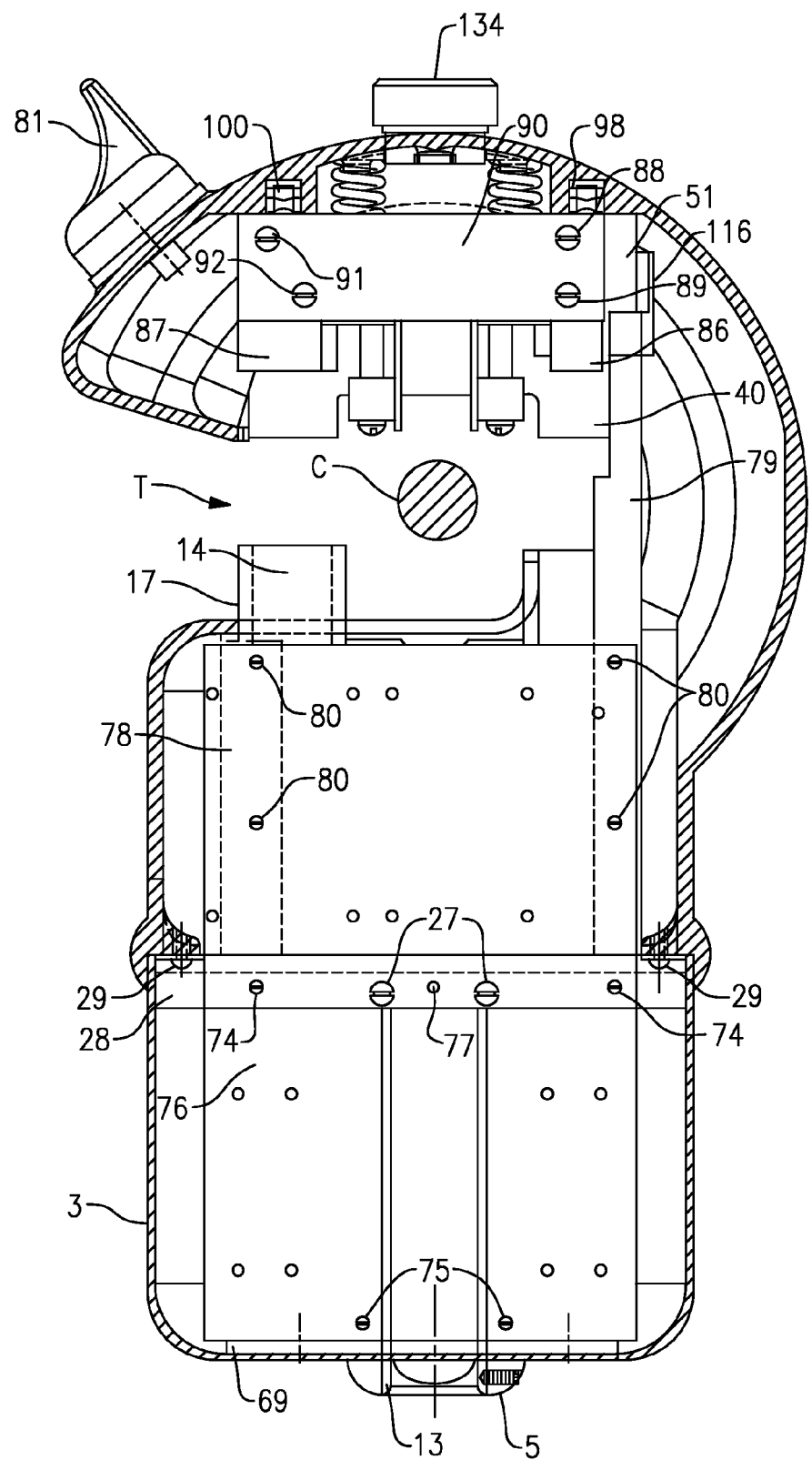
FIG. 12 illustrates a cross-sectional view taken along line B-B of FIG. 2.

The number of secondary turns $N_2$ of wire on the coil winding 56 are optimized to produce the required secondary voltage $V_2$ and secondary current $I_2$ with a minimum of current $I_1$ in the conductor C. The coil winding 56 is held in place by two coil bobbins 57 which are supported laterally by the two upper core blocks 43 and the two lower core blocks 44. Secondary leads 58*a* and 59*a* of coil windings 58 and 59, respectively, are connected to the power supply module 60 which maintains the same level of secondary voltage across leads 61 and 62 for the sensor electronics module 63 and the transmitter/receiver 64 even though the primary current may range from 34 amperes up to 1000 amperes. Lower primary currents of 6.8 amperes are achievable with the low threshold current power supply module 60. The power supply module 60 contains an energy storage device 256 (FIG. 13) which can power the transmitter/receiver 64 when the conductor C current ceases to flow. A transmitting and receiving antenna 81 for the on-board transmitter/receiver 64 is mounted on the upper housing 2 (FIG. 12).

Locating the coil winding 56, 58, and 59 on the upper magnetic core 40 allows the heat from the coil winding 56, 58, and 59 to escape through a vent 65 (FIG. 1) in the upper housing 2. When the conductor sensor S located within the STR unit 1 measures the temperature of the conductor C, it is important that the heat from the coil windings 56, 58, and 59 does not affect the temperature of the conductor C or the conductor temperature sensor S, which is in electrical communication with the sensor electronics module 63. As shown in FIG. 6, a thermally insulating barrier 66 located below the coil windings 56, 58, and 59, allows for a more accurate temperature reading of the conductor temperature by blocking heat from the coil windings 56, 58, and 59.

FIGS. 10-12 and 13 illustrate the lower magnetic core 14 with the lower core covers 17, the lead screw 22, the hotstick guide tube 13, and other related parts in both exploded and collapsed views. The hotstick guide tube 13 is anchored at the top with the through bolts 27 that extend through the bottom support 28 and the hotstick guide support 26. A round cylindrical milled slot 67 is located along opposing sides of the top of the hotstick guide tube 13 to accept the through bolts 27 that support the hotstick guide tube 13.

A central hole 70 extends through a base plate support 68 and a base plate 69 for accepting a bottom portion of the hotstick guide tube 13. The base plate support 68 and the base plate 69 are connected to each other with four identical threaded screws 71. The hotstick guide tube 13 is attached to the base plate support 68 and the base plate 69 with set screws 72 and 73. Left and right side panels 76 of FIG. 12 are attached to the base plate support 68 and the bottom support 28 for the lower core 14 with the use of two identical screws 74 extending through the bottom support 28 and the side panel 76 and at the bottom with two identical screws 75 extending through the side panel 76 and the base plate support 68.

The threaded bushing 25 rests on top of the hotstick guide tube 13 and is prevented from turning relative to the hotstick guide tube 13 using a set screw 77. The left and right side panels 76 not only provide added strength, but also provide the physical space to mount the power supply module 60, the transmitter/receiver 64, the sensor electronics 63, and support left and right lower core guides 78 and 79.

The left lower core guide 78 and a right lower core guide 79 are "U" shaped and guide the opening and closing mechanism 39 such that the lower magnetic core 14 is aligned with the upper magnetic core 40. Each of the left and right lower core guides 78 and 79 are attached to the left and right side panels 76 with four threaded screws 80. The lower housing 3 is placed over the hotstick guide tube 13 at the bottom and fitted up to the base plate 69 and held in place with the collar 5. This means that once the collar 5 is removed, the lower housing 3 can be removed thus allowing access to the power supply module 60, sensor electronics module 63, and the transmitter/receiver 64 of FIG. 9 mounted inside and on the left and right side panels 76 for easy maintenance and repair.

FIGS. 7 and 12-15 illustrate an upper magnetic core subassembly 40*a* mounted to the upper housing 2. The left and right core shoes 50 and 51 support the upper magnetic core 40 such that the upper magnetic core 40 can move freely up and down inside the left and right shoes 50 and 51. The left and right core shoes 50 and 51 are attached to the upper housing 2 using four support blocks 86 and 87 of FIG. 14, right and left upper core guides 90 and 93, and four vertical through bolts 94, 95, 96, and 97.

Figure 13:
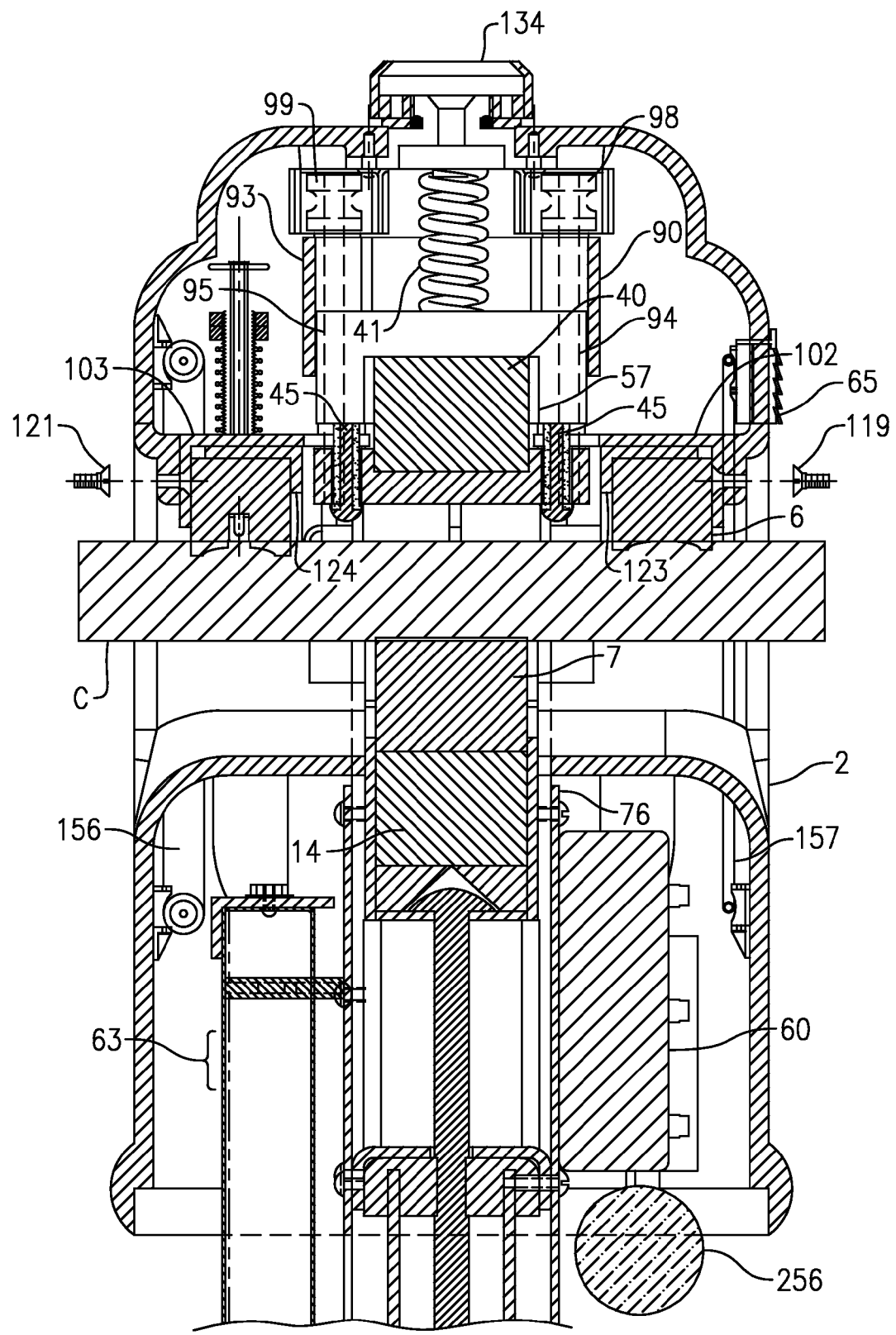
FIG. 13 illustrates a cross-sectional view taken along line C-C of FIG. 1.

The upper magnetic core subassembly 40*a* can be inserted through the throat T and fastened to the inside of the upper housing 2. A top portion of the upper housing 2 is "C" shaped which provides a surface on the inside for mounting a current sensing device 156 for measuring the power line frequency current (60 Hz or 50 Hz) and a loop coil 157 for measuring lightning stroke current (FIGS. 13 and 16).

The right core shoe 51 has two identical threaded holes 82 and 83 on the front and back for a total of four, and left core shoe 50 has two identical threaded holes 84 and 85 on the front and back for a total of four as shown in FIGS. 7 and 14. As shown in FIG. 14, two identical support blocks 86 on the right side are placed on the front and back of the right core shoe 51 and two identical support blocks 87 are placed on the front and back of the left core shoe 50.

To align the two right side support blocks 86 with the two sets of threaded holes 82 and 83 on the right side of the right core shoe 51, threaded screws 88 and 89 are first inserted into the upper and lower holes in the right side upper core guide 90 and then through the two holes in the right support block 86 and screwed into the accommodating threaded holes 82 and 83 of the right core shoe 51. The two left side support blocks 87 are held in alignment with the left core shoe 50 by first inserting two threaded screws 91 and 92 through the other end of the right side upper core guide 90 and then through the holes in the left side support block 87 and screwed into the threaded holes 84 and 85 of the left core shoe 50. The same process is repeated on the back side by connecting support blocks 86 and 87 to the left upper core guide 93 with the backside of the right core shoe 51 and the back side of the left core shoe 50.

The purpose of the upper core guides 90 and 93 is to insure the two long vertical through bolts 94 and 95 placed through the vertical holes in the two right side support blocks 86 and two long vertical through bolts 96 and 97 placed through the vertical holes in the two left side support blocks 87 line up with the four threaded holes in four threaded inserts 98, 99, 100, and 101, which are embedded in the casting of the upper housing 2. The two right side support blocks 86 are prevented from falling down by inserting the back of a right side upper jaw holder 102 and the back of the left side upper jaw holder 103 over the vertical through bolts 94 and 95 and threading nuts 104 and 105 onto the two vertical through bolts 94 and 95 and tightening them down, respectively. The two left side support blocks 87 are held in place by inserting the vertical through bolts 96 and 97 through the front hole in the right side upper jaw holder 102 and the front hole in the left side upper jaw holder 103 and threading two nuts 106 and 107 on the vertical through bolts 96 and 97 and tightening them down, respectively.

Four threaded through standoffs 108, 109, 110, and 111 are screwed onto the four vertical through bolts 94, 95, 96, and 97, respectively. The thermal barrier 66 is placed over the four bottom holes of the standoffs 108, 109, 110, and 111 and screwed to the standoffs 110 and 111 on the front left side with two flat head screws 112 as shown in FIG. 15.

Figure 15:
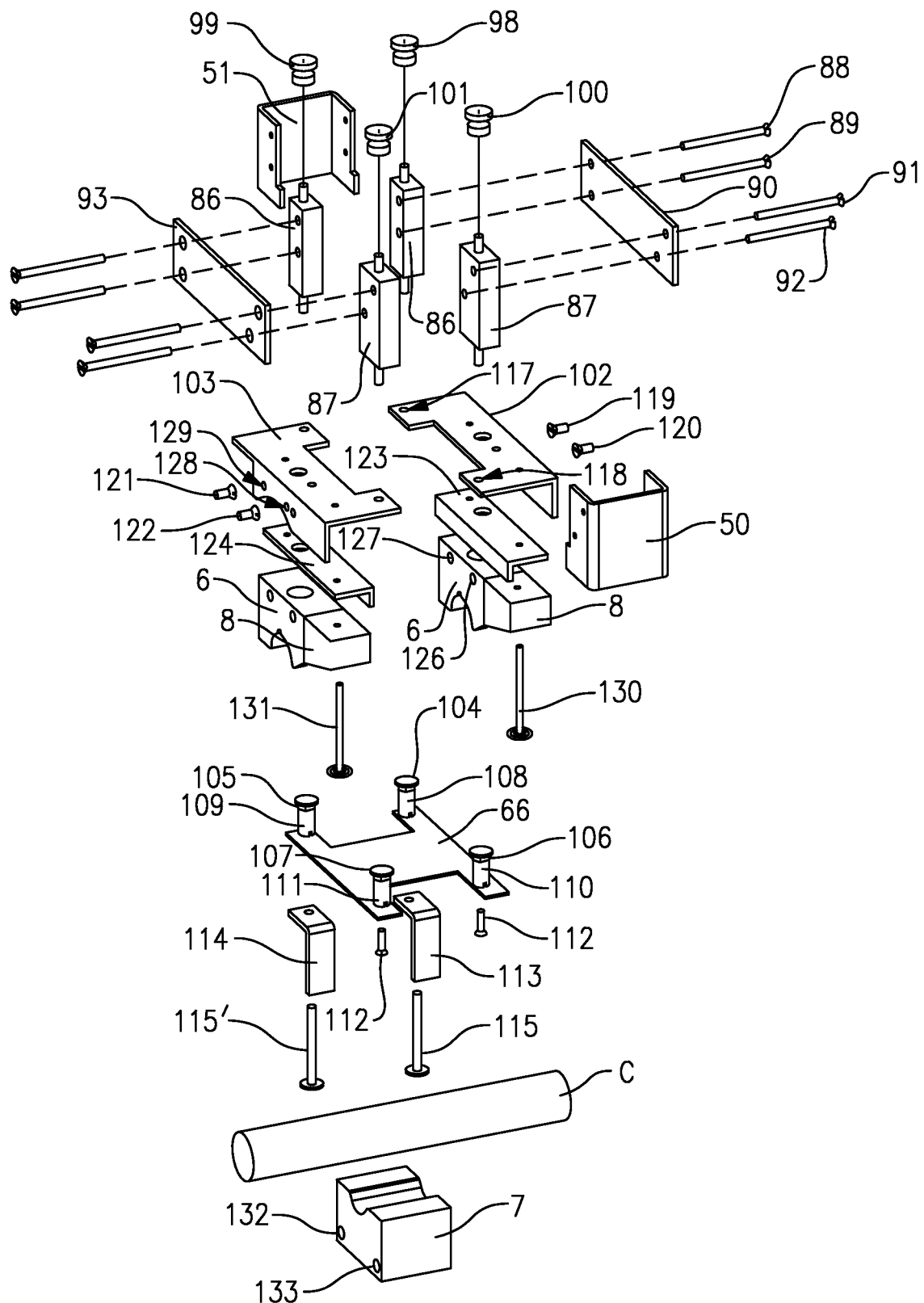
FIG. 15 illustrates an exploded view of an upper magnetic core mount and the upper and lower jaws.

FIGS. 2 and 15 illustrate casting fillers 113 and 114 located on the back left and back right sides of the STR unit 1 and secured with round head screws 115 which are first inserted through holes in the casting fillers 113 and 114 and then through the two back holes on the right and left side of the thermal barrier 66 and into the standoffs 108 and 109, respectively.

After the upper magnetic core subassembly 40a is mounted, the left and right lower core guides 78 and 79 including the opening and closing mechanism subassembly 39 and the left and right side panels 76 are inserted through the bottom of the upper housing 2 (See FIG. 12). Four screws 29 are inserted through the two holes on the left and the two holes on the right of the bottom support 28 and screwed into the threaded holes of the upper housing 2. It should be noted that during the insertion process, the right lower core guide 79, shown in FIG. 12, slides around the outside surface of the right core shoe 51 and underneath a tab 116 at the top as a weldment on the right upper side of the right core shoe 51.

As shown in FIG. 12, the tab 116 insures that the right lower core guide 79 fits precisely around the outside of the right core shoe 51 to provide a near perfect alignment of the lower magnetic core 14 with the upper magnetic core 40. The precise alignment between the upper magnetic core 40 and the lower magnetic core 14 reduces magnetic reluctance by decreasing the air gaps 54. This results in a decrease in the threshold current for the operation of the power supply module 60.

Referring to FIGS. 14 and 15, the right side upper jaw holder 102 and the left side upper jaw holder 103 support the two upper jaws 6 and the jaw inserts 8. The long vertical through bolts 96 and 97 which are screwed into the threaded inserts 100 and 101 at the top and on the inside of the upper housing 2 fit through top holes 117 and 118 on the back and front of the right side upper jaw holder 102 on the right side. Also, flush mount screws 119 and 120 are inserted on the back and through corresponding holes in the right side upper jaw holder 102 and are screwed into the upper housing. The flush mount screws 119 and 120 are installed before the upper jaws 6 and inserts 8 are mounted to the right side upper jaw holder 102. The same arrangement for mounting the left side upper jaw holder 103 is followed using screws 121 and 122.

Right and left upper jaw keepers 123 and 124 prevent the upper jaws 6 from dropping down on the inside, because spring pins 126 and 127 are located on the outside and when depressed snap into the holes 128 and 129 of the right side upper jaw holder 102. The same procedure is followed with the left upper jaw keeper 124.

The jaw inserts 8 on the right and left sides of the STR unit 1 and in front of the upper jaws 6 are held in place by inserting threaded bolts 130 and 131 into each insert 8 and through the right and left keepers 123 and 124 and screwing into the upper jaw holders 102 and 103. The spring pins 132 and 133 are included in the lower jaw 7 which when depressed snap into the two holes 15 in the lower jaw holder 16.

Figure 9:
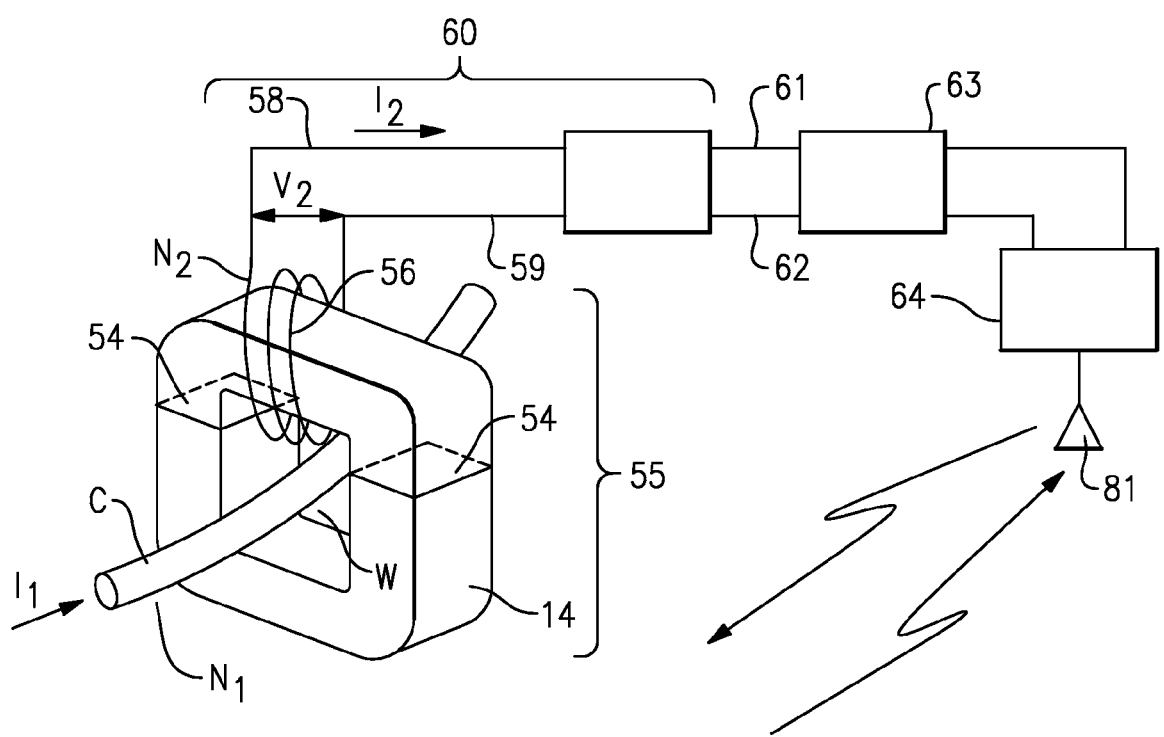
FIG. 9 illustrates a schematic view of the line mounted power supply, electronics and transmitter-receiver of the STR unit.

The transmitting and receiving antenna 81 for the on-board transmitter and receiver 64 shown in FIG. 9 is mounted on the housing 2. The antenna 81 is displayed in FIGS. 1 and 2 and is installed on the top left side in FIG. 1. The solar sensor assembly 134 is located at the top of this housing and on its vertical centerline (FIG. 13). The small hole 140 located directly to the right of the conductor 1 allows access and adjustment of the electric power line sag sensor 140 (FIG. 1).

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A device for attaching to an electric power line conductor comprising:
   a housing including an opening for accepting the power line conductor;
   a first jaw assembly and a second jaw assembly, the first jaw assembly and the second jaw assembly are located within the housing and are configured to engage the power line conductor, the first jaw assembly is fixed relative to the housing and the second jaw assembly is movable relative to the housing;
   a first magnetic core movable relative to the first jaw assembly including a first guide mechanism attached to the opposing sides of the housing configured to move the first magnetic core;
   a second magnetic core fixed to the second jaw assembly, the first magnetic core and the second magnetic core are configured to surround the power line, wherein the first magnetic core and the second magnetic core are configured to move in unison when in engagement until the second jaw assembly firmly clamps the power line conductor and the first jaw assembly and the second jaw assembly are configured to clamp onto power line conductors of different diameters while the first magnetic core and the second magnetic core are held together; and
   an actuator connected to the second jaw assembly and configured to move the second jaw assembly relative to the first jaw assembly.

2. The device of claim 1, wherein the first magnetic core is moveable along a track between at least one stop and at least one spring member.

3. The device of claim 2, wherein the first magnetic core and the second magnetic core are configured to move independently when separated.

4. The device of claim 1, wherein the first magnetic core is located on a first side of the opening in the housing and the second magnetic core is located on a second opposite side of the opening in the housing.

5. The device of claim 1, wherein said actuator and a support mechanism at least partially form an isolated fluid path configured to allow rain water to drain out of the housing.

6. The device of claim 1, wherein at least one of the first magnetic core and the second magnetic core includes a plurality of windings.

7. The device of claim 6, wherein the plurality of windings are in electrical communication with a power supply.

8. The device of claim 6, wherein the plurality of windings are in electrical communication with a power storage unit.

9. The device of claim 1, including a transmitter receiver configured to send and receive data.

10. The device of claim 1, including a second guide mechanism configured to move the second magnetic core.

11. The device of claim 10, wherein the second guide mechanism is attached to the opposing sides of the housing.

12. The device of claim 1, wherein the first jaw assembly includes a first inclined surface that is steeper than an inclined surface of a jaw insert adjacent the first jaw assembly.

13. The device of claim 1, wherein the second magnetic core is encased by a cover.

14. A method of attaching a device to a power line conductor comprising the steps of:
   a) resting a first jaw assembly on a power line conductor, the first jaw assembly fixed relative to a housing;
   b) moving a second jaw assembly toward the first jaw assembly with an actuator;

c) moving a second magnetic core toward a first magnetic core with the actuator, wherein the second magnetic core is fixed relative to the second jaw assembly and the first magnetic core is moveable relative to the first jaw assembly, the first magnetic core includes a first pair of distal ends and the second magnetic core includes a second pair of distal ends and the first pair of distal ends are configured to directly contact the second pair of distal ends when the first magnetic core and the second magnetic core move in unison; and d) moving the first magnetic core and the second magnetic core relative to the first jaw assembly until the first jaw assembly and the second jaw assembly firmly clamp the power line conductor, wherein the first jaw assembly and the second jaw assembly can accommodate power line conductors of varying diameter.

15. The method of claim 14, wherein step b) further includes turning a screw in a first direction to move the second jaw assembly toward the first jaw assembly.

16. The method of claim 14, wherein the first magnetic core and the second magnetic core surround the power line conductor.

17. The method of claim 15, including biasing the first magnetic core against a spring member.

18. The method of claim 14, wherein step a) further includes sliding the power line conductor across inserts fixed to the housing including a first inclined surface before sliding the power line conductor across the first jaw assembly including a second inclined surface, an angle of incline of the second inclined surface is greater than an angle of incline of the first inclined surface.

19. The device of claim 1, wherein the first magnetic core includes a first pair of distal ends and the second magnetic core includes a second pair of distal ends and the first pair of distal ends are configured to directly contact the second pair of distal ends when the first magnetic core and the second magnetic core move in unison.

20. The device of claim 19, wherein the first magnetic core and the second magnetic core are U-shaped.

21. The device of claim 11, wherein the opposing sides of the housing are fixed from movement relative to each other.

22. The method as recited in claim 14, wherein the first magnetic core and the second magnetic core are configured to move in unison when in direct contact until the second jaw assembly firmly clamps the power line conductor and the first jaw assembly and the second jaw assembly are configured to clamp onto power line conductors of different diameters while the first magnetic core and the second magnetic core are in direct contact.

* * * * *